United States Patent
Cimino

(10) Patent No.: US 7,905,918 B2
(45) Date of Patent: Mar. 15, 2011

(54) ELASTIC METALLIC REPLACEMENT LIGAMENT

(75) Inventor: William Wayne Cimino, Louisville, CO (US)

(73) Assignee: William Wayne Cimino, Louisville, CO (US)

( * ) Notice: Subject to any disclaimer, the term of this patent is extended or adjusted under 35 U.S.C. 154(b) by 238 days.

(21) Appl. No.: 11/895,015

(22) Filed: Aug. 23, 2007

(65) Prior Publication Data

US 2009/0054982 A1 Feb. 26, 2009

(51) Int. Cl.
*A61F 2/08* (2006.01)

(52) U.S. Cl. .......... 623/13.19; 623/13.11; 623/13.13; 623/13.14

(58) Field of Classification Search ...... 623/13.11–13.2, 623/23.54
See application file for complete search history.

(56) References Cited

U.S. PATENT DOCUMENTS

| | | | |
|---|---|---|---|
| 4,127,902 A | 12/1978 | Homsy | |
| 4,149,277 A | 4/1979 | Bokros | |
| 4,187,558 A | 2/1980 | Dahlen | |
| 4,209,859 A | 7/1980 | Hoffman | |
| 4,246,660 A | 1/1981 | Wevers | |
| 4,255,820 A | 3/1981 | Rothermal | |
| 4,301,551 A | 11/1981 | Dore | |
| 4,345,339 A * | 8/1982 | Muller et al. | 623/13.2 |
| 4,584,722 A | 4/1986 | Levy | |
| 4,642,119 A | 2/1987 | Shah | |
| 4,662,886 A | 5/1987 | Moorse | |
| 4,728,329 A | 3/1988 | Mansat | |
| 4,792,336 A * | 12/1988 | Hlavacek et al. | 623/13.18 |
| 4,795,466 A | 1/1989 | Stuhmer | |
| 4,834,755 A | 5/1989 | Silvestrini | |
| 4,917,700 A | 4/1990 | Aikins | |
| 5,002,574 A * | 3/1991 | May et al. | 623/13.13 |
| 5,004,474 A | 4/1991 | Fronk | |
| 5,018,969 A * | 5/1991 | Andreiko et al. | 433/20 |
| 5,078,745 A | 1/1992 | Rhenter | |
| 5,263,984 A * | 11/1993 | Li et al. | 623/13.18 |
| 5,383,925 A | 1/1995 | Schmitt | |
| 5,749,919 A * | 5/1998 | Blanc | 623/1.22 |
| 6,827,743 B2 | 12/2004 | Eisermann | |
| 2002/0040241 A1* | 4/2002 | Jarvinen | 623/13.14 |
| 2004/0024457 A1* | 2/2004 | Boyce et al. | 623/13.17 |

OTHER PUBLICATIONS

McCulloch, P.C., et al., "An illustrated history of anterior cruciate ligament surgery", J. Knee Surg., Apr. 2007, 20(2): 95-104.

* cited by examiner

*Primary Examiner* — Thomas J Sweet
*Assistant Examiner* — Yashita Sharma
(74) *Attorney, Agent, or Firm* — Marsh Fischmann & Breyfogle LLP

(57) ABSTRACT

This invention relates generally to orthopedic implants for reconstruction of severed, ruptured, or damaged ligaments. More particularly, this invention relates to an improved elastic replacement ligament made from metallic wires in a braided construction for replacement of a natural ligament of the body such as the anterior cruciate ligament of the knee.

41 Claims, 7 Drawing Sheets

ELASTIC METALLIC REPLACEMENT LIGAMENT

CROSS-REFERENCE TO RELATED APPLICATIONS

Not Applicable

STATEMENT REGARDING FEDERALLY SPONSORED RESEARCH

Not Applicable

REFERENCE TO SEQUENCE LISTING, TABLE, OR COMPUTER PROGRAM

Not Applicable

FIELD OF THE INVENTION

This invention relates generally to orthopedic implants for reconstruction of severed, ruptured, or damaged ligaments. More particularly, this invention relates to an improved elastic replacement ligament made from metallic wires in a braided construction for replacement of a natural ligament of the body such as the anterior cruciate ligament of the knee.

BACKGROUND OF THE INVENTION

The anterior cruciate ligament (ACL) joins the femur and the tibia bones of the leg such that functional motion and stability are maintained in the human knee joint. Other ligaments, specifically the collateral ligaments and the posterior cruciate ligament (PCL), participate in the stabilization of the knee joint but the ACL is considered to be the primary mechanical link between the femur and the tibia, thus indicating its importance to the proper overall function of the knee joint. Because the ACL (and the PCL) have poor intrinsic ability to heal, tears in these ligaments are most often treated with surgical reconstruction (replacement of the ligament) using biologic autografts such as, for example, the patellar tendon graft, the hamstring tendon graft, or the quadriceps tendon graft. Autografts require surgical harvesting of the graft from a tendon the patient, which produces pain and a scar at the harvest site, as well as post-operative discomfort. The tendon that is selected for the autograft may be weakened as a result of the removal a part of its structure. However, the autograft is the 'gold-standard' for ACL repair today as alternative graft methods have not yet produced results that hold up over time and that provide the stability and flexibility needed for a successful reconstruction.

Alternative graft methods include the allograft graft and the synthetic graft. Allografts are replacement grafts taken from cadavers. These are not in wide use today due to limited supply, the risk of disease transmission, and possible rejection by the body.

A synthetic, or artificial, replacement ligament graft would be desirable because it would eliminate the harvest portion of the surgery and all associated pain and scars, and weakening of the harvest tendon (harvest site morbidity). Additionally, a synthetic replacement ligament would reduce the overall surgery time because the harvest portion of the surgery would not be necessary. Further, the rehabilitation period following surgery would be significantly reduced due to the elimination of the trauma resulting from the harvest portion of the surgery.

Ideally, the properties of a replacement ligament graft, such as for the ACL, would mimic or reasonably approximate the characteristics of the normal biological ACL such as strength, elasticity, and durability. Published studies (Woo, S. L., et al., "Tensile properties of the human femur-anterior cruciate ligament-tibia complex", Am. J. Sports Med., 1991, 19(3):217-225; Noyes, F. R., et al., "Biomechanical analysis of human ligament grafts used in knee-ligament repairs and reconstructions", J. Bone and Joint Surg., 1984, 66:344-352) of human ACL strength show rupture strengths in the range 388 pounds (1725 N, Noyes) to 486 pounds (2160 N, Woo) and axial (longitudinal) stiffness in the range 1040 pounds per inch (182 kN/m, Noyes) to 1668 pounds per inch (292 kN/m, Woo). Any replacement ligament graft must also be durable enough to provide many years of function and must be biocompatible.

Several approaches to synthetic replacement grafts have been attempted. Designs that have been tried include polymeric and non-metallic textile materials such as polyethylene (Polyflex ligament), polytetrafluoroethylene (Gore-Tex replacement ligament), polyethylene terephthalate (Dacron; Stryker-Meadox and Leeds-Keio replacement ligaments), carbon fibers (Integraft replacement ligament), and polypropylene (Kennedy Ligament Augmentation Device) (McCulloch, P. C., et al., "An illustrated history of anterior cruciate ligament surgery", J. Knee Surg., April 2007, 20(2): 95-104). The rupture strength and axial stiffness of these synthetic replacement grafts are summarized in the chart below, along with values for natural ACL ligaments. Clinical evaluations and long-term follow-up of ACL reconstructions using these synthetic replacement ligaments have generally shown poor long-term results due to persistent pain, synovitis (inflammation of the lining of a joint), sterile effusions (non-infected leaking of fluid), arthritis, and mechanical breakdown of the replacement materials (McCulloch, P. C., et al., "An illustrated history of anterior cruciate ligament surgery", J. Knee Surg., April 2007, 20(2): 99). Further, these replacement ligaments are subject to mechanical problems such as creep (gradual stretching under load) and fatigue failure due to cyclic loading. While several of these replacement ligaments received conditional approval by the United States Food and Drug Administration for evaluation in the 1980's and 1990's, none of these devices have received unconditional FDA approval for primary ACL reconstruction and none of these devices are commercially available today in wide distribution, primarily due to poor long-term performance and the undesirable complications listed above. Current research is directed primarily at tissue engineering approaches to ligament replacement.

Rupture Strength and Axial Stiffness of Synthetic ACL Grafts

|  | Natural ACL | Gore-Tex | Dacron | Leeds Keio | KLAD |
|---|---|---|---|---|---|
| Rupture Strength (N) | 1725-2160 | 5300 | 3600 | 2000 | 1500 |
| Axial Stiffness (kN/m) | 182-292 | 320 | 420 | 280 | 280 |

Synthetic ligaments made from biocompatible textile materials are disclosed in patents. U.S. Pat. No. 5,078,745 to Rhenter has a replacement ligament for the knee consisting of two independent bundles of fibers made of polyester, polypropylene, or glass, and arranged in a crossing formation. U.S. Pat. No. 4,795,466 to Stuhmer has an artificial ligament for the knee that has a least three layers of concentric tubular textile structures which bifurcate to form a pair of branches.

U.S. Pat. No. 4,834,755 to Silvestrini has a prosthesis of triaxially-braided polymeric materials including polyester, polyether, polyethylene terephthalate, and polyethylene. U.S. Pat. No. 4,917,700 to Aikins has a prosthetic ligament that includes a braided jacket over an unbraided core. U.S. Pat. No. 5,004,474 to Fronk has an artificial ligament with a woven design made of lower melting point polymers such as styrene-ethylene/butylene and higher melting point polymers such as polyethylene terephthalate and with at least one end region encased within a polymeric bone block for attachment purposes. U.S. Pat. No. 4,792,336 to Hlavacek has braided ligament or tendon with fibers parallel to the implant length, made of glycolic acid ester and trimethylene carbonate linkages. None of these patents disclose an elastic metallic replacement ligament or a means to make an elastic metallic replacement ligament with elasticity and strength properties appropriate for replacing a natural ligament of the body such as the ACL in the human knee.

The use of a woven mesh for use as an orthopedic implant is disclosed in patents. U.S. Pat. No. 6,827,743 to Eisermann has an orthopedic implant made of mesh materials, including metal, wherein the network of woven fibers is substantially nonelastic for stabilizing or immobilizing bone fractures or bone segments, as an alternative to stiff metal plates, and such that the mesh implant promotes bone ingrowth and bone fusion during the healing process. The nonelastic mesh is a woven design of single interconnecting fibers that form a flat mesh material that is formed into desired shapes, with each fiber joined to an adjacent fiber at a juncture. This patent does not teach or suggest the use of metallic wires organized in a braided construction, nor does it teach or suggest the use of metallic wires for a replacement ligament that spans a moveable joint of the body such that the natural motion of said moveable joint is maintained. Further, bone ingrowth into the wire mesh implant, as taught in the Eisermann patent, to stabilize bone fractures or repair bone defects, is not desirable in the present invention because such bone ingrowth would cause the replacement ligament to loose its flexibility, thus making it nonfunctional.

BRIEF SUMMARY OF THE INVENTION

It has been discovered that it is possible to produce an elastic replacement ligament made of metallic wires organized in a braided construction such that the elastic replacement ligament generally emulates the elasticity and strength properties of a natural ligament of the body. While braiding with metallic wires is known for different medical purposes, for example, tubular braid designs for catheter wall reinforcement and stiffening; it is not obvious that a braid of metallic wires could be created with the desired elastic properties of a natural ligament such as, for example, the anterior cruciate ligament of the knee. This is evident given the above described history of synthetic replacement ligaments failures which are based on polymeric or textile materials, or carbon fibers, all of which are, in general, much more flexible than metallic materials for a given size or geometry. As a further example that it is not obvious that a braid of metallic wires could be created with the desired elastic properties of a natural ligament, it is instructive to consider wire ropes. Wire ropes are constructed of metal wires and are available in a variety of diameters and rope patterns. A 7×7 stainless steel wire rope pattern with a total diameter of $1/16^{th}$ of an inch (1.58 mm) has a rupture strength of 480 pounds (2133 Newtons) (Wire Rope Corporation of America, data sheet for minimum breaking force and weight for 7×7 utility cable, www.wrca.com/wr_specialty.html), in the range of the natural ACL as indicated above. The effective modulus (elastic tensile property) of a wire rope has been measured for various wire ropes and reported to be between 59%-62% of the elastic modulus of the steel wires from which the rope is made (Costello, G. A., *Theory of Wire Rope*, $2^{nd}$ ed., Springer, New York City, N.Y., 1997, p 72, 78), depending on the size and design of the wire rope and the percent of maximal loading. Thus, the axial stiffness of the $1/16^{th}$ inch wire rope cited above is estimated to be in the range 54,000-57,000 pounds per inch (9,450-9,975 kN/m). The result is that the $1/16^{th}$ inch wire rope axial stiffness is more than 40 times the midrange value of the reported axial stiffness of the natural ACL (1,350 lb/in, 236 kN/m), making it inappropriate, and not functional, for consideration as a replacement ligament. Furthermore, the bending stiffness of the wire rope would be greatly in excess of the natural ACL, again making it inappropriate and non-functional for use as a synthetic ligament.

While the disclosed elastic metallic replacement ligament may be constructed using any appropriate biocompatible metallic wire material, such as, for example, a stainless steel alloy, the preferred metallic material is titanium or a titanium alloy. Titanium and titanium alloys possess superior biocompatibility characteristics and are frequently and commonly used in the body as the base metal material for many different implant applications such as bone screws and bone fixation hardware. Titanium and titanium alloys also possess superior fatigue properties when compared to other metals and also have a modulus of elasticity that is about 56% of the modulus of elasticity of stainless steel, thus making them much more flexible than stainless steel. This combination of biocompatibility, fatigue, and elasticity properties make titanium and titanium alloys particularly applicable to the fabrication of an elastic metallic replacement ligament. However, a simple construction of biocompatible metal wires with sufficient strength for a replacement ligament, such as for replacement of the ACL, will have inherent stiffness properties that makes them inappropriate for use in an application that requires both the axial elastic properties (in the direction of longitudinal extension) of a natural ligament and bending flexibility (in a direction perpendicular to longitudinal extension). This design requirement has been resolved in the present invention by using metallic wires, preferably of titanium or a titanium alloy, with a very small diameter or thickness, and organized in a braided construction. It is now possible to produce very small diameter metallic wires of titanium or titanium alloy, for example, a titanium alloy wire, with a diameter 0.005 inches (0.127 mm) or smaller, depending on the titanium alloy chosen. These individual metallic wires do not possess the required strength for a replacement ligament, but a large number of these metallic wires can be organized in a braided construction that possesses both the required strength and elasticity properties for an elastic metallic replacement ligament.

It is, among other desirable attributes, an overall object of the present invention to provide an elastic metallic replacement ligament for replacement of a damaged natural ligament or ligament of the body.

It is a further object of the present invention to provide an elastic metallic replacement ligament that eliminates the need for harvest surgery of other tissues of the body to be used for ligament reconstruction or replacement, and thereby eliminating associated harvest site morbidity.

It is a still further object of the present invention to provide an elastic metallic replacement ligament that reduces overall surgical time and expense by eliminating the harvest portion of the surgery.

It is yet still a further object of the present invention to provide an elastic metallic replacement ligament with strength and elasticity properties that reasonably emulate the properties of the natural ligament to be replaced.

It is yet still a further object of the present invention to provide an elastic metallic replacement ligament that is biocompatible and that possesses fatigue properties such that the replacement ligament is well tolerated by the body and does not creep, rupture, or break due to large numbers of various loading cycles.

It is yet still a further object of the present invention to provide support devices for tunnels in the bone that prevent undesirable wear and stress between the elastic metallic replacement ligament and the bone.

It is yet still a further object of the present invention to provide termination devices that hold and lock the elastic metallic replacement ligament in place and provide a means of adjusting tension in the elastic metallic replacement ligament.

It is a final object of the present invention to provide a method of making an elastic metallic replacement ligament to replace a damaged natural ligament of the body.

BRIEF DESCRIPTION OF THE DRAWINGS

The novel features of the present elastic metallic replacement ligament are set forth in the appended claims. The elastic metallic replacement ligament will be best understood by reference to the following figures when read in conjunction with the detailed description of the elastic metallic replacement ligament.

DETAILED DESCRIPTION OF THE INVENTION

The apparatus and method disclosed herein are directed toward achieving the aforementioned objects of the present elastic metallic replacement ligament.

In order to produce a useful elastic replacement ligament made from small diameter metallic wires, a way of reducing axial stiffness and bending stiffness, while maintaining sufficient strength, is required. A braided construction accomplishes these objectives and maintains the necessary strength such that the elastic replacement ligament does not rupture or exceed the elastic or strength limitations of any of the metallic wires used in the construction. The following terms are defined for purposes of clarity, but not as any limitation.

Wire: a thin, long filament of a selected metal. In the present invention all wires are considered to be metallic. Wires may have a generally round cross-section, an oval cross-section, or a generally rectangular cross-section.

Strand: a bundle of wires (more than one wire) where the wires in the bundle may be parallel to each other, or twisted together, or braided together. Strands may then be braided together to create a greater braided structure.

Braid: a structure of wires or wire strands where the wires or wire strands are interlaced in an overlapping pattern. A braid requires a minimum of three strands or three wires. In this specification a braid is considered to have a longitudinally extending axis that defines the intended longitudinal (or axial) loading direction. The wires in the braided construction extend generally the length of the braid and terminate at or near the two ends of the braid. Several different braid patterns are possible, having different numbers of and organization of strands.

Axial stiffness: a measure of the elastic properties in the axial direction, i.e., along the longitudinal or extensional aspect, usually expressed in units of pounds per inch or Newtons per meter. A kN/m is 1,000 Newtons per meter.

Figure 6:
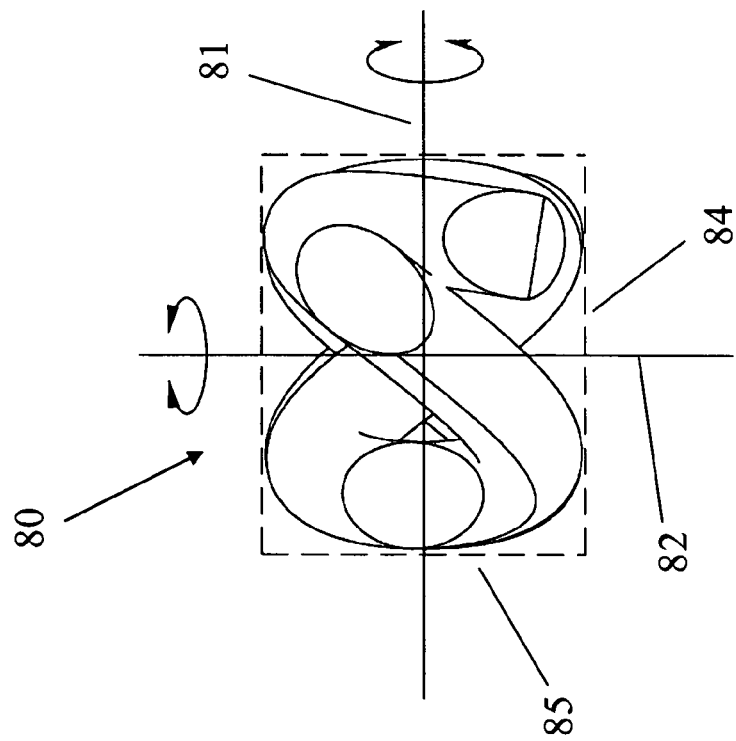
FIG. 6 shows a cross-sectional view of a 3-wire flat braid construction and the generally rectangular shape of the cross-section.

Bending stiffness: a measure of the elastic properties in a direction perpendicular to the longitudinal or extensional aspect. Bending stiffness may be measured about any axis perpendicular to the longitudinal axis, but is generally measured about an axis that is perpendicular to the longitudinal axis and which is specified relative to a geometric feature of a cross-section. For example, a round cross-section has generally equal bending stiffness in all directions, whereas a rectangular cross-section would have reduced bending stiffness about an axis containing the long dimension of the rectangle and increased bending stiffness about an axis containing the shorter dimension of the rectangle, as seen in FIG. 6.

Rupture strength: the strength or load at which a ligament, either natural or synthetic, breaks. Rupture strength may also be called ultimate strength or failure strength, and is measured in the axial or longitudinal direction. Rupture strength is usually expressed in units of pounds or Newtons.

Yield strength: the strength or load at which wires in an elastic metallic replacement ligament undergo permanent unrecoverable deformation by elongation. Yield strength is usually expressed in units of pounds or Newtons.

Figure 1:
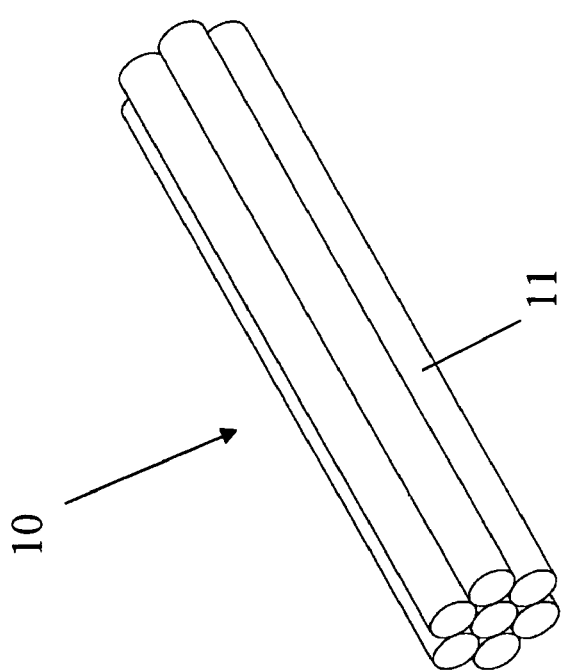
FIG. 1 shows a perspective view of a portion of a strand constructed of 7 individual wires, the wires organized in a generally parallel construction.

Referring to the drawings, FIG. 1 shows a portion of a strand 10 constructed of seven individual wires. One wire 11 is labeled in the Figure. The wires are organized such that they are generally parallel to each other along the length of the strand. Practical issues of manufacturing and assembly dictate that the wires will not remain exactly parallel to each other but may shift or be otherwise slightly displaced relative to a perfectly parallel arrangement. A strand constructed in this manner may have any number of wires and does not have to be of a generally round cross-section as shown in FIG. 1. When strands of this type are used in a braided construction, the wires in the strand will shift to accommodate stresses and bends present in the braided construction.

Figure 2:
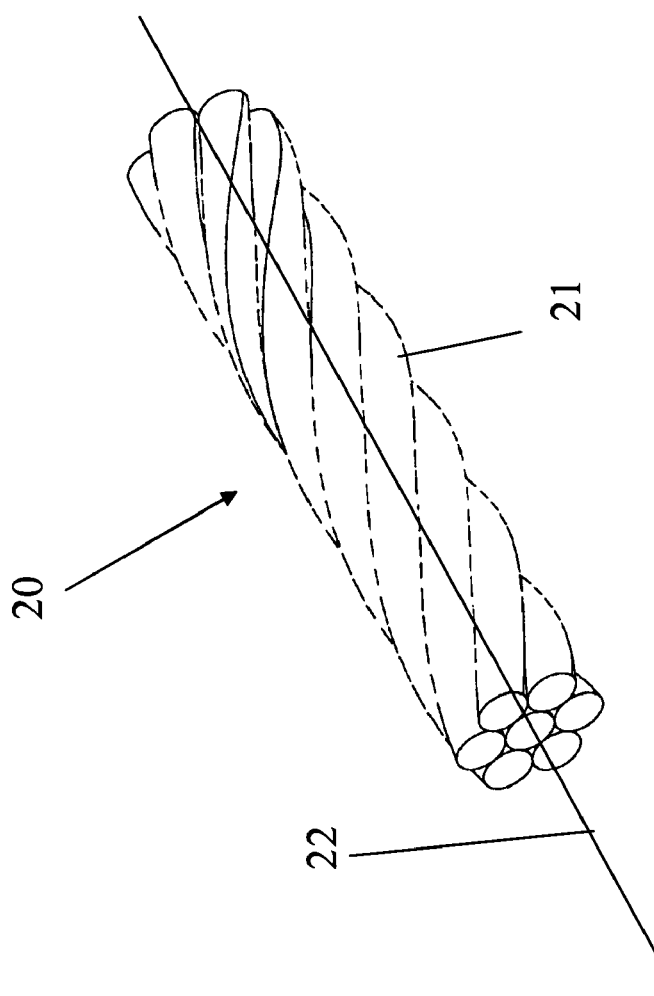
FIG. 2 shows a perspective view of a portion of a strand constructed of 7 individual wires, the wires organized in a twisted construction.

FIG. 2 shows a portion of a strand 20 constructed of seven individual wires. One wire 21 is labeled in the Figure. The wires are organized such that they twist about a longitudinal central axis 22 of the strand. A strand constructed in this manner may have any number of wires twisted together and does not have to be of generally round cross-section as shown in FIG. 2. When strands of this type are used in a braided construction, the wires in the strand will shift to accommodate stresses and bends present in the braided construction, but will retain a twisted organization.

Figure 3:
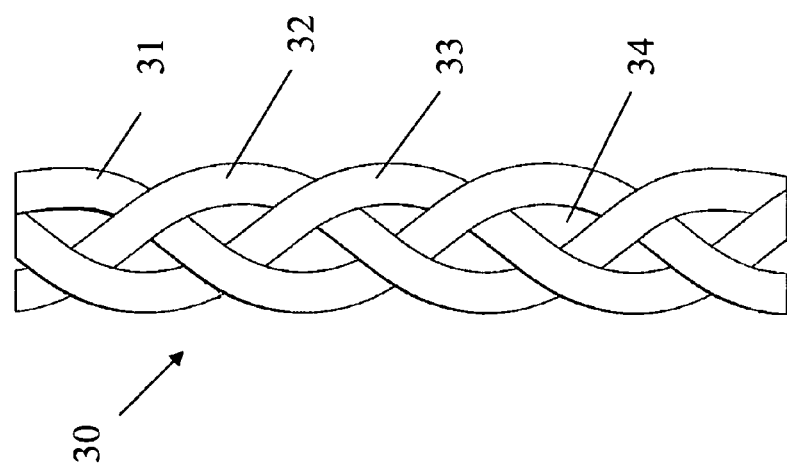
FIG. 3 shows a perspective view of a portion of a strand constructed with three wires, the wires organized in a 3-wire flat braid construction.

FIG. 3 shows a portion of a braided strand 30 that is constructed using three wires. The three separate wires are identified in the Figure as 31, 32, and 33. FIG. 3 shows how three wires are interlaced in an overlapping pattern to form a braided construction that may be a strand used in a greater braid or may be the final braided form. The braid shown in FIG. 3 is a 'loose' construction, meaning that significant space 34 is shown between the braid wires. The same braid pattern can be produced such that it is much tighter, where most or all of the space between wires is eliminated, and the wires fit tightly together in the braid pattern. The braid shown in FIG. 3 is constructed with three single wires. Such a braid pattern could also be constructed with strands made of many wires. If a braid pattern such as that shown in FIG. 3 is constructed of strands made of many wires (see FIG. 5), then the number of wires in the braid would be the number of wires in each strand multiplied by three (three strands are shown).

Figure 5:
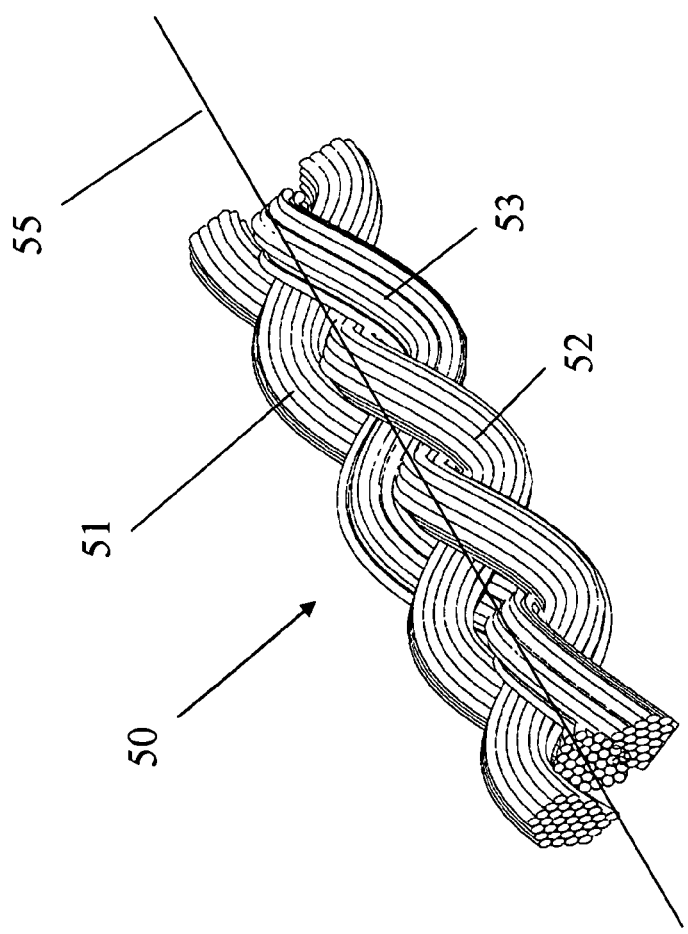
FIG. 5 shows a perspective view of a portion of an elastic metallic replacement ligament with 3 strands organized in a flat braid construction, each of the 3 strands having many wires organized in a generally parallel construction.

Other braid patterns such as, for example, 4, 5, 6, 8, or 12 wire (or strand) braid patterns may be used. The braided construction shown in FIG. 3 would be considered a flat braid pattern, having a generally rectangular cross-section that is approximately three wires wide and one to two wires tall, due to the undulating and overlapping course of the wires in the braid pattern. Such a braid pattern could also be constructed using strands of wires, as shown in FIG. 5. A four strand flat braid would have a cross-section that is approximately four strands wide and one to two strands tall, again due to the undulating and overlapping course of the wires in the braid pattern. Analogously, a five strand flat braid would have a cross section that is approximately five strands wide and one to two strands tall. It is understood that the interlacing of the strands or wires in a braid requires that the strand, or wire, undulate up and down and back and forth along the length of the braid. Thus, while it is stated above that a three wire flat braid has a cross-section that is approximately three wires wide and one to two wires tall, it will be understood that the width of the braid may be slightly more or less than precisely three wires wide, and the height (tallness) of the braid may be slightly more or less than precisely one to two wires high, due to the undulation and overlapping of the braided wires. The same understanding would apply to width and height of braids constructed with strands. Flat braids may also have more than one layer of wires or strands (increased height), as long as the width of the braid is also correspondingly increased. For example, a braid that is six strands wide and two strands tall would be considered a flat braid because the finished braid would be wider than it is tall. Flat braid constructions are more flexible bending in the thin aspect of the flat braid than in the wide aspect of the flat braid. Round and square braid patterns have generally round and generally square cross-sections, respectively. For example, a four-strand square braid pattern would have a cross-section with strands organized in a two-wide and two-tall arrangement. Such patterns are well known and familiar to those experienced with braid technology.

Figure 4:
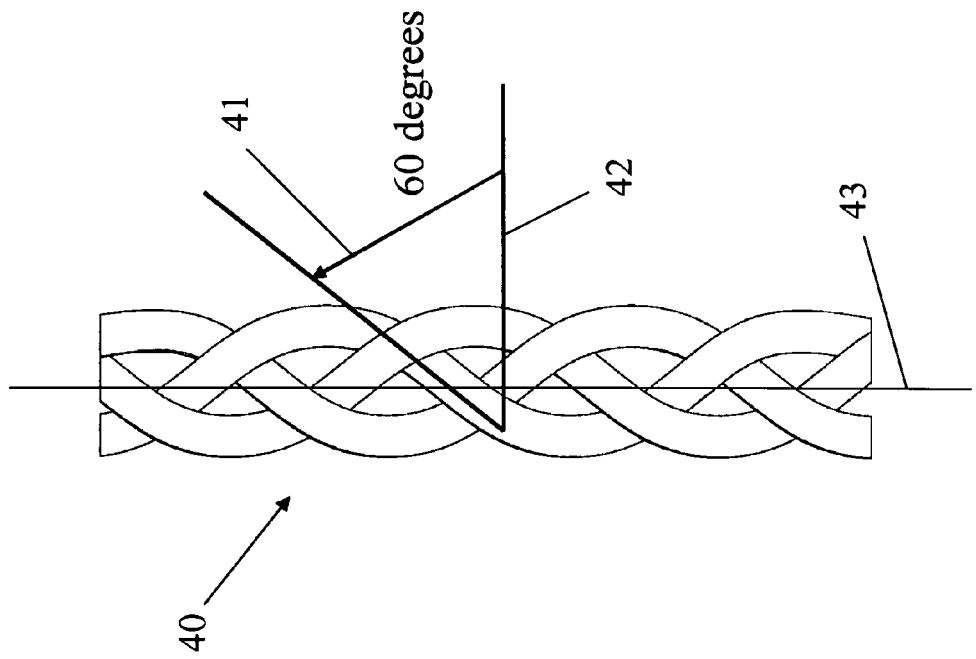
FIG. 4 shows a portion of strand constructed using a 3-wire flat braid pattern with an indication of the approximate braid angle.

FIG. 4 shows a portion of a three-wire braid 40 with an indication of the concept of braid angle 41. The braid angle for the braid shown in FIG. 4 is approximately 60 degrees, measured from a line 42 perpendicular to the long axis 43 of the braid. The braid angle 41 indicates the approximate angle of the wire or the strand as it crosses from one side of the braid to the other side. The concept of braid angle applies to individual wires as shown in FIG. 4 and also to strands used in a braided construction, as shown in FIG. 5. As the braid angle approaches 90 degrees the strands or wires become more and more parallel to the long axis 43 of the braid and the braid properties increasingly reflect those of parallel strands or parallel wires. As the braid angle decreases, the strands or wires become more oriented to a direction transverse to the long axis of the braid and the axial stiffness of the braid decreases. Thus, the braid angle may be increased or decreased to achieve different axial stiffness (along the long axis 43) characteristics in the braid. Decreasing the braid angle also affects the bending stiffness, generally reducing the bending stiffness as the braid angle is decreased.

FIG. 5 shows a portion of an elastic metallic replacement ligament 50 made of metallic wires organized in three strands of generally parallel wires, the three strands identified as 51, 52, and 53, respectively. The three strands are braided together in a flat braid pattern (three strands wide, one to two strands tall) to create the elastic metallic replacement ligament. Other braid patterns such as, for example, 4, 5, 6, 8, or 12 strand braid patterns may be used. The preferred embodiment is a flat braid of strands where the strands have a generally parallel construction (as shown in FIG. 1) as this reduces the number of wire over wire contact points yet still produces the required flexibility and strength. The strands may alternatively be twisted strands or braided strands as shown and described in FIGS. 2 and 3. The three-strand braid pattern shown in FIG. 5 has a longitudinal axis 55.

FIG. 6 shows a cross-sectional view 80 of a three-wire flat braid, such as those shown in FIGS. 3 and 4, with the generally rectangular shape of the cross-section indicated with a dashed line. The cross-section view 80 has a width 84 (dashed line) and height (or tallness) 85 (dashed line). In this example the flat braid construction is three wires, or strands, wide, and one to two wires, or strands, tall (height), i.e., the width is greater than the height. The cross-sectional view 80 shows that the width is actually slightly greater than three wires or strands, and that the height (or tallness) is actually slightly greater than one wire or strand, as described above. A width transverse axis 81 that is perpendicular to the longitudinal axis 43 (FIG. 4), parallel to the width of the cross-section, and in the plane of the cross-section, is shown. A height transverse axis 82 that is perpendicular to the longitudinal axis 43 (FIG. 4), parallel to the height of the cross-section, and in the plane of the cross-section, is also shown. The bending stiffness about the width transverse axis 81 (direction shown by rotation arrows) is less than the bending stiffness about the height transverse axis 82 (direction shown by rotation arrows). This is an inherent property of rectangular cross-sections assuming nominally homogeneous material properties.

Figure 7:
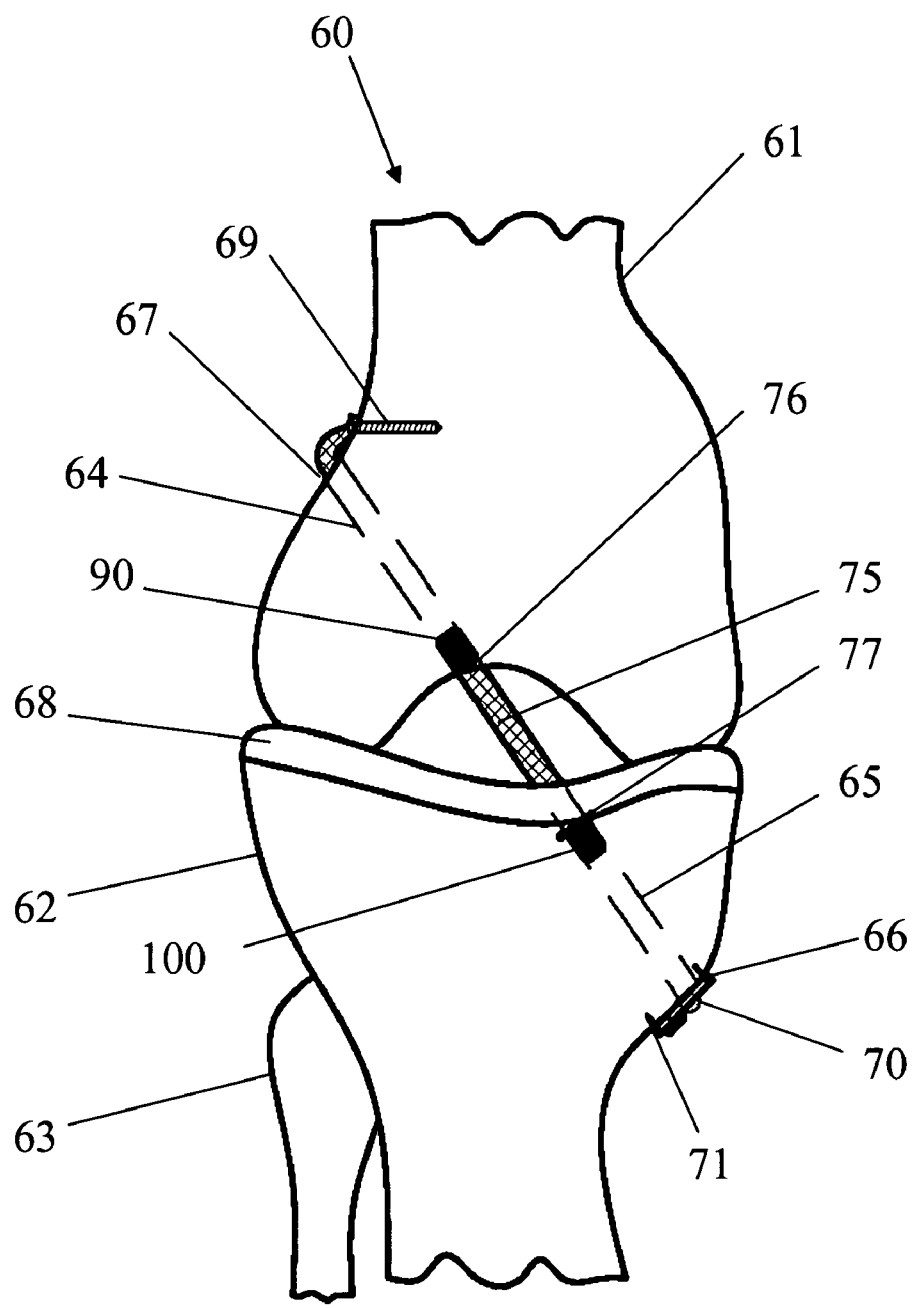
FIG. 7 is a diagrammatic representation of a human knee showing a possible placement of an elastic metallic replacement ligament, and tunnels in the femur and tibia bones.

FIG. 7 shows a diagrammatic representation of a human knee 60 as seen from the front. The femur 61, the tibia 62, and the fibula 63 bones are shown. Cartilage layer 68 separates the heads of the two bones 61 and 62 and provides a lubricious contact surface therebetween for smooth joint motion. A tunnel 64 in the femur 61 and a tunnel 65 in the tibia 62 are used for placement of the elastic metallic replacement ligament 75. The elastic metallic replacement ligament 75 may span the entire lengths of tunnels 64 and 65 and be anchored at the exit point 66 of tunnel 65 (distal end), and at the exit point 67 of tunnel 64 (distal end), and the joint between an entrance point 76 of tunnel 64 and an entrance point 77 of tunnel 65. One end or a first portion of the replacement ligament 75 must be attached to the femur 61 and the other end or a second portion of the replacement ligament must be attached to the tibia 62. Attachment may be accomplished with any suitable anchoring technique such as, for example, interference fixation screws, synthetic or bone plugs, locking mechanisms at the distal reach of the channel or tunnel, or screw posts that penetrate the bone and lock the replacement ligament at the distal reach of a channel or tunnel or at some other location between the two ends of the channel or tunnel. Staples and sutures may also be used; however these tend to fail at lower load levels. Attachment techniques as described above and variations thereof are well known to orthopedic surgeons and there are several commercially available products and instruments to provide said means of attachment. As one example, a screw post 69 is shown pinning the elastic metallic replacement ligament to the femur 61 near the exit point 67 of tunnel 64. As a second example, the other end of the elastic metallic replacement ligament is shown attached to the tibia 62 with a tunnel termination plate 70 and a screw post 71. A tunnel termination plate is a mechanical device that holds and locks the replacement ligament at the exit of the tunnel so that the replacement ligament does not slip and so that it does not abrade the edges of the tunnel exit. A perspective view of one design for a termination plate is shown in FIG. 10, and is more fully described below. The elastic metallic replacement ligament is threaded through the tunnel termination plate 70 which is attachable to the bone using the screw posts such that the replacement ligament is held and locked in place. Several forms or designs for a termination plate are possible as long as they appropriately hold and lock the elastic metallic replacement ligament, and in cooperation with a means to attach the termination plate to the bone, hold the elastic metallic replacement ligament in place and prevent the elastic metallic replacement ligament from slipping. The tunnel termination plate may be fabricated from biocompatible metals such as commercially pure titanium with grades 1, 2, 3, or 4, or titanium alloys of the group Ti6Al/4V, Ti6Al/4V ELI, Ti3Al/2.5V, or Ti6Al/7Nb, or nickel-titanium alloys, or stainless steels of the group with designations including 302, 303, 304, or 316. In the preferred embodiment the termination plate would be made of the same metal as the elastic metallic replacement ligament to prevent galvanic interactions therebetween. A threaded tunnel support sleeve 90 (details shown in FIG. 9) is shown at the entrance point 76 of tunnel 64 and a barbed tunnel support sleeve 100 (details shown in FIG. 8) at the entrance point 77 of tunnel 65. The barbed tunnel support sleeve 100 is recessed into the bony surface using a counterbore. The threaded tunnel support sleeve 90 is screwed into the tunnel 64 until the top of the sleeve is approximately flush with or slightly recessed with respect to the bony/cartilage surface.

Figure 8B:
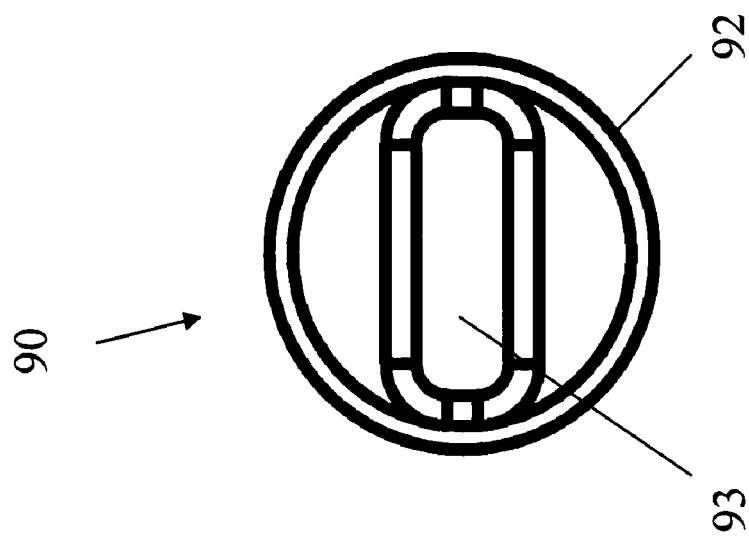
FIGS. 8a and 8b show a perspective view and an end view of a barbed tunnel support sleeve, respectively.
Figure 8A:
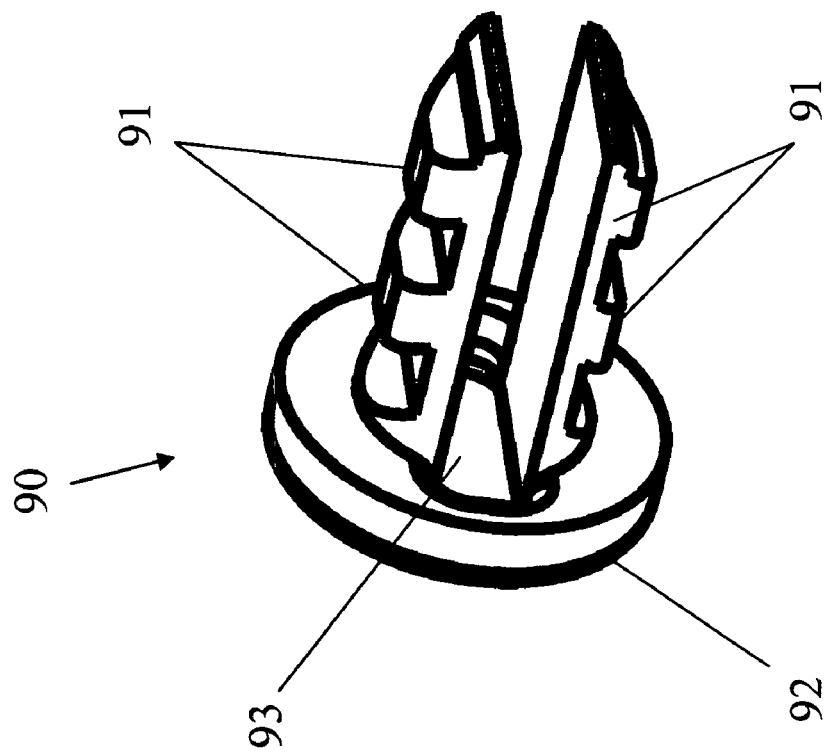

FIGS. 8*a* and 8*b* are a perspective and an end view of a barbed tunnel support sleeve 90, respectively. The bone and tissues at entrance point 76 of tunnel 64 and at entrance point 77 of tunnel 65 (FIG. 7) are subject to stress and abrasion from the elastic metallic replacement ligament 75 as the knee flexes. Conversely, the elastic metallic replacement ligament is subject to stress and abrasion from the bone. A tunnel support sleeve may be used to provide a means to protect and maintain the bone, tissues, and the elastic metallic replacement ligament at these entrance points. The barbed tunnel support sleeve 90 is inserted into the entrance of the bone tunnel and held in place by barbed engagements 91. Other types of engagement with the bone may be used such as screw threads or bone cement. The barbs of the tunnel support sleeve 90 may be coated or have a surface to promote bony ingrowth to better hold and lock the tunnel support sleeve into place. The barbed tunnel support sleeve 90 has a head 92 with an opening 93 for passage of the elastic metallic replacement ligament therethrough. The head 92 may sit at the top of the tunnel or a counterbore may be used to recess the head 92 such that the head is flush with the top of the tunnel at its respective entry point. The opening 93 is shaped to accommodate the shape of the elastic metallic replacement ligament. For example, the opening 93 shown in FIGS. 8*a* and 8*b* is generally rectangular and would be used for a flat braid with a generally rectangular cross-section. The tunnel support sleeve may be made of biocompatible metals such as commercially pure titanium with grades 1, 2, 3, or 4, or titanium alloys of the group Ti6Al/4V, Ti6Al/4V ELI, Ti3Al/2.5V, or Ti6Al/7Nb, or nickel-titanium alloys, or stainless steels of the group with designations including 302, 303, 304, or 316. In the preferred embodiment the tunnel support sleeve would be made of the same metal as the elastic metallic replacement ligament to prevent galvanic interactions therebetween. A tunnel support sleeve may also be used at the distal ends of the tunnels (the exit points 66 and 67 in FIG. 7) to support the bony structure at those locations.

Figure 9B:
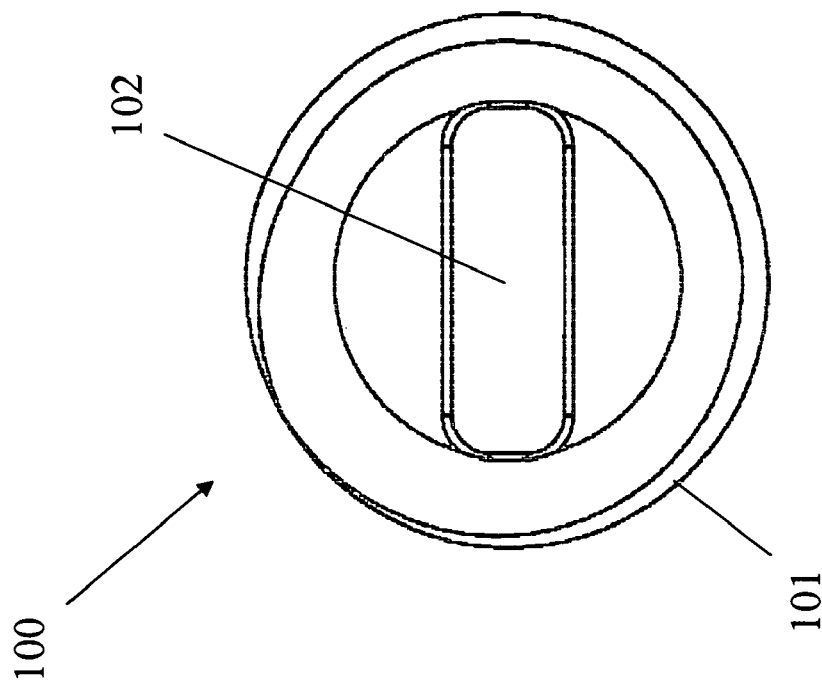
FIGS. 9a and 9b show a perspective view and an end view of a threaded tunnel support sleeve, respectively.
Figure 9A:
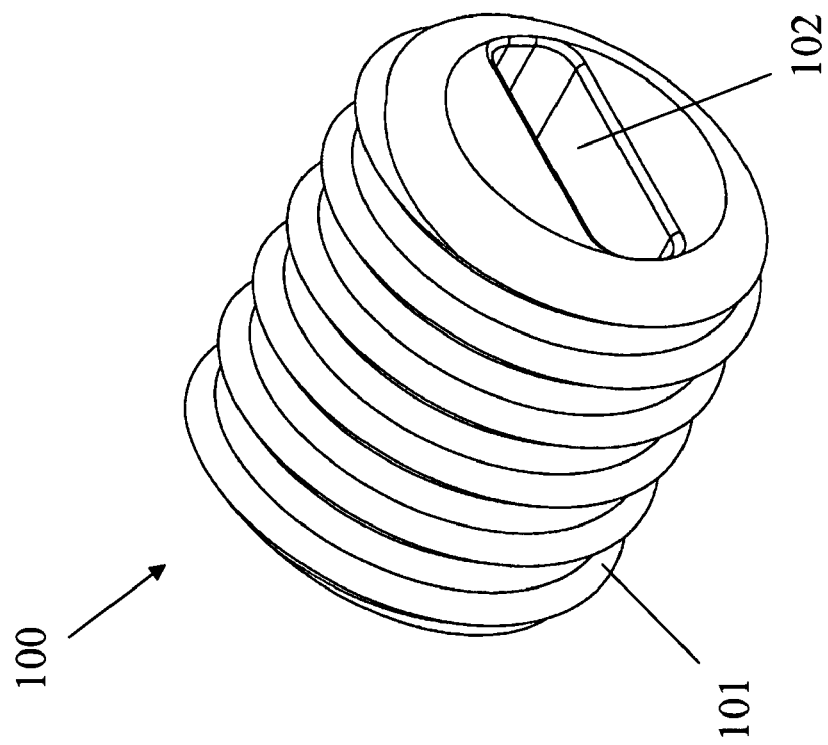
Figure 10:
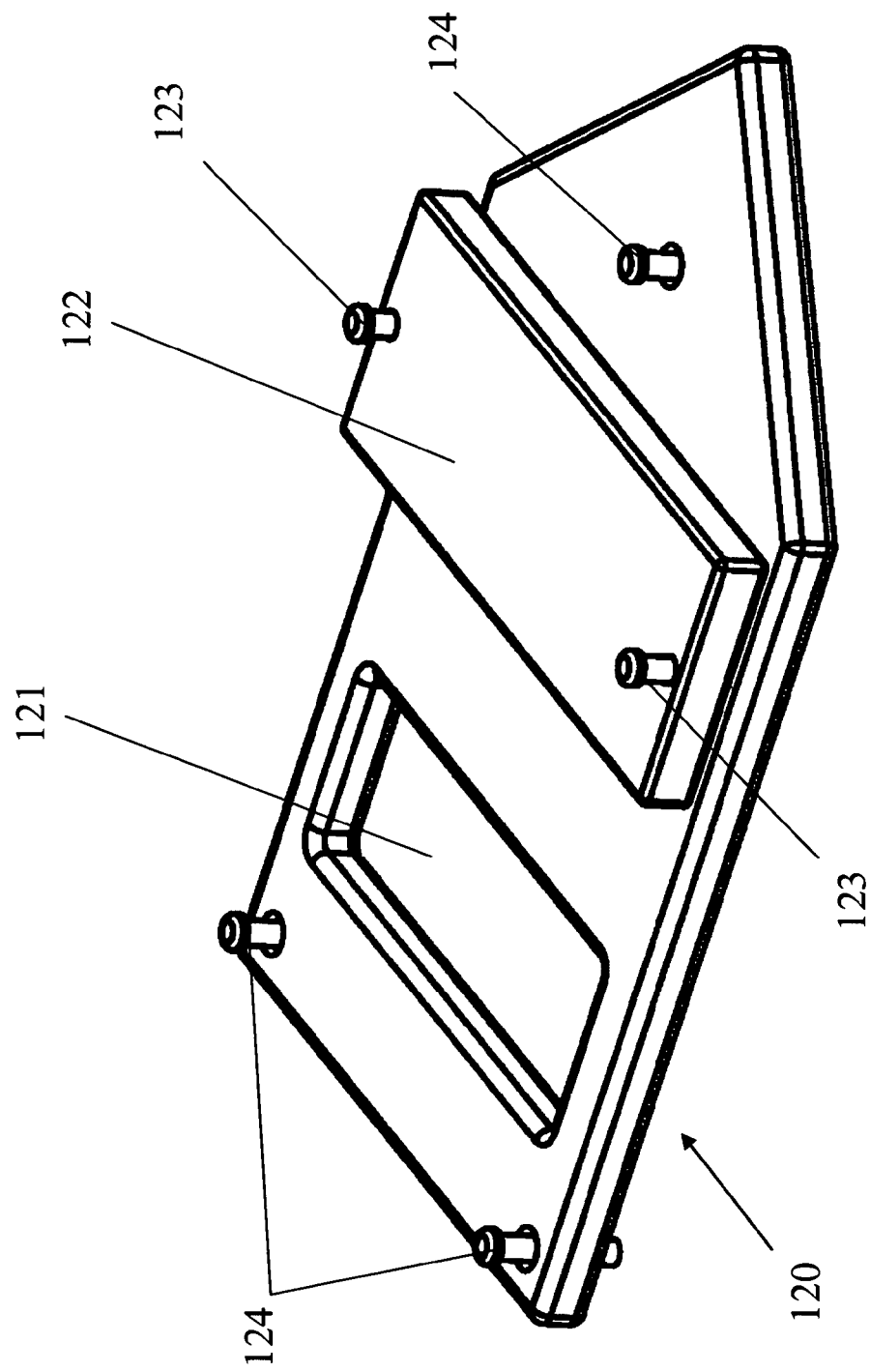
FIG. 10 is a perspective view of one design for a tunnel termination plate.

FIGS. 9*a* and 9*b* are a perspective and an end view of a threaded tunnel support sleeve 100, respectively. The bone and tissues at entrance point 76 of tunnel 64 and at entrance point 77 of tunnel 65 (FIG. 7) are subject to stress and abrasion from the elastic metallic replacement ligament 75 as the knee flexes. Conversely, the elastic metallic replacement ligament is subject to stress and abrasion from the bone. A threaded tunnel support sleeve 100 may be used to provide a means to protect and maintain the bone, tissues, and elastic metallic replacement ligament at these entrance points. The threaded tunnel support sleeve 100 is screwed in to the entrance of the tunnel and held in place by screw threads 101. Other types of engagement with the bone may be used such as barbs or bone cement. The threads of the tunnel support sleeve 100 may be coated or have a surface to promote bony ingrowth to better hold and lock the tunnel support sleeve into place. The tunnel support sleeve has an opening 102 for passage of the elastic metallic replacement ligament therethrough. The opening 102 is shaped to accommodate the shape of the elastic metallic replacement ligament. For example, the opening 102 shown in FIGS. 9*a* and 9*b* is generally rectangular and would be used for a flat braid with a generally rectangular cross-section. The tunnel support sleeve may be made of biocompatible metals such as commercially pure titanium with grades 1, 2, 3, or 4, or titanium alloys of the group Ti6Al/4V, Ti6Al/4V ELI, Ti3Al/2.5V, or Ti6Al/7Nb, or nickel-titanium alloys, or stainless steels of the group with designations including 302, 303, 304, or 316. In the preferred embodiment the tunnel support sleeve would be made of the same metal as the elastic metallic replacement ligament to prevent galvanic interactions therebetween. A tunnel support sleeve may also be used at the distal ends of the tunnels (the exit points 66 and 67 in FIG. 7) to support the bony structure at those locations.

FIG. 10 shows a perspective view of one design for a tunnel termination plate 120. The tunnel termination plate 120 is attached to the bone near or at the tunnel exit points 66 or 67 (FIG. 7) and used to fix or lock the elastic metallic replacement ligament in place. The tunnel termination plate 120 has an opening 121 through which the elastic metallic replacement ligament is passed. In the preferred embodiment, the elastic metallic replacement ligament is threaded under a clamp piece 122 and then locked in place by clamping the clamp piece 122 on the ligament using locking screws 123. The tunnel termination plate is attached to the bone with screws 124. The tunnel termination plate may be bent or shaped to match the shape of the bone where it is attached. Variations on the design of a tunnel termination plate are possible. For example, screws may be used to clamp the elastic metallic replacement ligament directly between a tunnel termination plate and the bone, or screws may be located so that they penetrate through the elastic metallic replacement ligament, or the tunnel termination plate may have multiple openings so that the elastic metallic replacement ligament may be looped through the multiple openings. The tunnel termination plate may be made of biocompatible metals such as commercially pure titanium with grades 1, 2, 3, or 4, or titanium alloys of the group Ti6Al/4V, Ti6Al/4V ELI, Ti3Al/2.5V, or Ti6Al/7Nb, or nickel-titanium alloys, or stainless steels of the group with designations including 302, 303, 304, or 316. In the preferred embodiment the tunnel termination plate would be made of the same metal as the elastic metallic replacement ligament to prevent galvanic interactions therebetween. One significant advantage of the tunnel termination plate when used with an elastic metallic replacement ligament is that the tension in the replacement ligament may be adjusted. The embodiment as shown in FIG. 10 has a means of adjusting the tension in the replacement ligament by moving the replacement ligament forward or backward under the clamp piece 122, then tightening the clamp piece 122 with locking screws 123. The tension in the elastic metallic replacement ligament may be adjusted at the time of initial surgery. The tension in the replacement ligament may also be adjusted at some time after surgery by opening the skin over the tunnel termination plate to expose said termination plate, then loosening the locking screws 123, adjusting the tension in the elastic metallic replacement ligament, and retightening the locking screws 123 to lock the elastic metallic replacement ligament in place.

In general, an elastic metallic replacement ligament for connection between two different bones to stabilize a movable joint therebetween is disclosed. Use of such a replacement ligament requires that one end or a first portion of the replacement ligament be attached to one bone on one side of the movable joint and that the other end or a second portion of the replacement ligament be attached to the second bone on the other side of the movable joint. A movable joint is a joint such as a knee or elbow or shoulder joint where large angular motions may occur between the two bones connected at the movable joint. For example, a knee joint allows the upper leg (femur) and the lower leg (tibia with fibula) to move from a straight position (leg extended) to more than ninety degrees of flexion (knee bent).

The elastic metallic replacement ligament disclosed herein includes metallic wires organized in a braided construction. The individual metallic wires may have a diameter or thickness between 0.0005 inches (0.013 mm) and 0.005 inches (0.127 mm). There are a variety of different braid constructions or patterns that may be used, including round braid constructions with generally round (or tubular) cross-sections, or flat braid constructions with generally rectangular cross-sections. Round cross-sections provide designs with uniform bending stiffness in all bending directions while rectangular cross-sections (flat braids) provide a bending stiffness in one transverse direction that is significantly less than in the other transverse direction. FIG. 5 shows a flat braided construction using three strands where the cross-section would be generally rectangular.

Two or more individual metallic wires may be grouped into a strand such that the metallic wires are generally parallel along their lengths as shown in FIG. 1. Alternatively, two or more individual metallic wires may be grouped into a strand such that the metallic wires are twisted together as shown in FIG. 2, or three or more individual metallic wires may be grouped together in a strand such that the metallic wires are braided together as shown in FIG. 3. Strands of these types may then be used in a greater braided construction to form the final elastic metallic replacement ligament. A braid construction requires a least three strands or wires; use of only two strands or wires results in a simple twisting of the two strands or wires together.

In the preferred embodiment the metallic wires are made of titanium or titanium alloy such as, for example, commercially pure titanium with grades 1, 2, 3, or 4, or titanium alloys of the group Ti6Al/4V, Ti6Al/4V ELI, Ti3Al/2.5V, or Ti6Al/7Nb. The metallic wires may also be made of nickel-titanium alloy or other biocompatible metals such as stainless steel, for example, of the group with designations including 302, 303, 304, or 316. To achieve the desired elasticity for the replacement ligament, the individual metallic wires must have a diameter or thickness between 0.0005 inches (0.013 mm) and 0.005 inches (0.127 mm). If the diameter is greater than the upper limit of 0.005 inches (0.127 mm) then the metallic wire will have a stiffness that will not permit the construction of an elastic metallic replacement ligament with the necessary elastic and strength properties. The individual metallic wires may have a round cross-section as, for example, a round wire, or a generally rectangular cross-section. Slightly oval cross-sections are also possible and may be desirable in some braided constructions. In such a case the minor diameter of the individual metallic wires should be between 0.0005 inches (0.013 mm) and 0.005 inches (0.127 mm).

A tunnel support sleeve, as described above and shown in FIGS. 8a, 8b, 9a, and 9b, is used to minimize stress and wear interactions between the elastic metallic replacement ligament and the bone. By minimizing stress and wear interactions the durability of both the elastic metallic replacement ligament and the supporting bone are increased. A tunnel support sleeve may be located at or in the end of any bone tunnel where the elastic replacement ligament exits the tunnel. Thus, it is possible with two bone tunnels, one tunnel in each bone, to have up to a maximum of four tunnel support sleeves, two in each tunnel. The tunnel support sleeves also have the beneficial attribute that they partially seal the ends of the bone tunnels, limiting the amount of debris or particles that may enter or exit the tunnels.

A tunnel termination plate, as described above and shown in FIG. 10, is used to lock or fix one or both ends of the elastic metallic replacement ligament to the respective bones. A tunnel termination plate may be used to lock or fix each end of the elastic metallic replacement ligament to the respective bones, or a tunnel termination plate may be used to lock or fix one end of the elastic metallic replacement ligament to one bone and an alternate means, such as a fixation screw, may be used to lock or fix the other end of the elastic metallic replacement ligament to the other bone. The tunnel termination plate allows the tension in the elastic metallic replacement ligament to be adjusted, either at the time of surgery when the end of the elastic metallic replacement ligament is being attached or fixed to the bone, or at some time after surgery. Adjustment at some time after surgery may be desired due to changes in the joint condition, stretch or elongation of the elastic metallic replacement ligament, or a less than optimal tensioning at the time of the initial surgery. The design for the tunnel termination plate shown in FIG. 10 uses a simple clamp mechanism to lock the elastic metallic replacement ligament to the tunnel termination plate, which is then attached to the bone. Other design approaches to locking or fixing the elastic metallic replacement ligament to the tunnel termination plate are possible, and included within the spirit of this invention, so long as the elastic metallic replacement ligament is locked or fixed to the tunnel termination plate such that the elastic metallic replacement ligament is held securely by the tunnel termination plate which is attached to the bone, and such that said ligament is not damaged so that durability is compromised, and such that the tunnel termination plate allows a surgeon to set tension in the elastic metallic replacement ligament.

The functions of the tunnel support sleeve and the tunnel termination plate, described herein as separate entities for purposes of clarity, may be combined into a single entity serving both purposes. As one example, the barbed tunnel support sleeve shown in FIGS. 8a and 8b could be fabricated integrally with the tunnel termination plate shown in FIG. 10. In such a design the functions of both the tunnel support sleeve and the tunnel termination plate would be maintained.

In general it is desirable that the axial yield strength of the elastic metallic replacement ligament exceed, or at a minimum, closely approximate the axial rupture strength of the natural ligament to be replaced. To utilize axial yield strength of a significantly lesser value would lead to potential premature failure and decreased performance. It is also desirable that the axial stiffness of the elastic metallic replacement approximate the axial stiffness of the natural ligament to be replaced so that the replacement ligament recipient achieves function as close as possible to conditions prior to replacement of the damaged natural ligament. Because the axial stiffness of a natural ligament cannot be assessed after it is damaged in any particular patient, and because the axial stiffness of a selected natural ligament may vary significantly from patient to patient, it is therefore best to characterize the axial stiffness for a selected natural ligament using a range based on measured values from a number of patients. Thus, in the preferred embodiment, the axial stiffness of the elastic metallic replacement ligament should be in a range between one-half to two times the axial stiffness of the natural ligament to be replaced. The axial stiffness of the elastic metallic replacement ligament should not exceed the range between one-third to three times the axial stiffness of the natural ligament to be replaced.

A method of making an elastic metallic replacement ligament is also disclosed. The method comprises the steps: (a) selecting metallic wires, preferably of titanium or titanium alloy, with a diameter or thickness in the range 0.0005 inches (0.013 mm) to 0.005 inches (0.127 mm); (b) organizing the metallic wires into strands; (c) braiding the strands such that an elastic metallic replacement ligament is formed with the desired strength and stiffness properties.

The wires and strands used to make a braided construction result in decreased axial stiffness relative to a non-braided straight wire construction for two primary reasons. First, for a given required overall length for a replacement ligament, a braided construction incorporates longer individual wires or strands than the straight wires used in a non-braided straight construction. The individual wires or strands in a braided construction undulate back and forth and in and out due to the overlapping and interleaving aspect of the braid, resulting in a greater length of wire to achieve the required overall length for a replacement ligament. The axial stiffness is inversely proportional to the length of the wires or strands. Thus, as the wires or strands get longer the axial stiffness is decreased. Second, the wires and stands in a braided construction have a degree of limited motion, and thus can move relative to one another when the braid is placed under axial tension or undergoes bending. Specifically, the strands or wires become more aligned with the long axis of the braid due to axial tension, which has the effect of increasing the braid angle. With increasing tension, the strands or wires of a braid achieve a 'locking angle' where the relative motion of the strands or wires cease and the braid becomes locked. Prior to locking, the axial stiffness of the braid is much less than the axial stiffness after the locking angle is achieved, due primarily to the relative motion of the strands or wires. Thus, a braid can be understood to have properties that create an axial stiffness before locking that can be much less than the axial stiffness after locking. The elongation prior to locking is sometimes referred to as constructional stretch, while the elongation after locking is sometimes referred to as elastic stretch. As a braid is placed under increasing axial tension, the axial stiffness of the braid transitions from the initial axial stiffness (constructional stretch) to the increased axial stiffness after locking occurs (elastic stretch). The braid stiffness prior to and after locking is a function of many variables in the braid construction including, for example, the braid angle, the tension in the braid wires or strands, the braid pattern, and the diameters of the wires or strands relative to the size of the finished braid, and the number of wires in the braid. By controlling such variables it is possible to design a braid such that the axial stiffness after locking (elastic stretch) is achieved is a few times the axial stiffness before locking (constructional stretch), or such that the axial stiffness after locking is achieved is many times the axial stiffness before locking. The above described properties of a braided construction are used, in cooperation with the described materials and specified diameters, to construct an elastic metallic replacement ligament with the desired stiffness and strength properties to emulate a natural ligament of the body.

NUMERICAL EXAMPLE

The following numerical example is intended to show the feasibility of an elastic metallic replacement ligament for ACL reconstruction and outline the basic steps for the design of an elastic metallic replacement ligament for ACL reconstruction. Skilled artisans with knowledge of the disclosure herein will understand and be able to make the present elastic metallic replacement ligament. Many other design choices, other than those described below, could be made to achieve different desired results for an elastic metallic replacement ligament. The following calculations are approximate and intended to guide the design process for the particular application selected. The final physical properties of such an elastic metallic replacement ligament would need to be measured and evaluated after construction to determine actual strength and stiffness properties. The design process and design calculations can then be appropriately adjusted and the design iterated until the desired final result is obtained.

For the present example it is desirable to start with an elastic metallic replacement ligament with an initial yield strength that exceeds the natural ACL rupture strength by a safety factor of 1.33 (33% over-design). Using the two sources of published data cited above, the mid-range estimate for natural ACL rupture strength is around 450 pounds (2,000 N). Incorporating the safety factor of 1.33, the targeted initial yield strength for the elastic metallic replacement ligament is then about 600 pounds (2,660 N). A round titanium alloy wire is selected with a diameter of 0.003 inches (0.076 mm). Other wire diameters or materials may be chosen. Such a titanium alloy wire may typically have a yield strength of 100,000 pounds per square inch (688,970 kN/m$^2$) and an elastic modulus of 16,000,000 pounds per square inch (110,235,000 kN/m$^2$). As a starting point, assume all wires are in a single bundle parallel to the longitudinal axis of the intended braid (braid angle equal to 90 degrees), and a uniform load distribution among the wires. Then a total of 849 wires with the 0.003 inch (0.067 mm) diameter, organized as indicated above, would be needed to achieve an initial yield strength of about 600 pounds (2,660 N).

In this numerical example it is assumed that the elastic metallic replacement ligament will be attached to the femur and tibia bones at the distal ends 66 and 67 of the tunnels 65 and 64, respectively, using screw posts and/or tunnel termination plates (refer to FIG. 7). Screw posts (an example shown as 69 in FIG. 7) fix the elastic metallic replacement ligament to the bone by clamping the replacement ligament between the bone and the head of the screw post. For this numerical example, a natural, adult ACL is assumed to have a length of around one inch (25 mm) that spans the knee joint from the tibia to the femur, shown as the cross-hatched portion 75 in FIG. 7, which would vary from patient to patient. Each bone tunnel (64 and 65 in FIG. 7) is assumed to have a length of about one and one-eighth inches (27 mm), which would also vary from patient to patient. Thus, in this example, the loaded length of the elastic metallic replacement ligament would be about, 3.25 inches (7.62 cm); comprising the one inch (25 mm) spanning the joint and about one and one-eighth inches (27 mm) in each bone tunnel (64 and 65 in FIG. 7). The axial stiffness of this single bundle of parallel wires can be estimated using AS=N*E*A/L, where AS is the axial stiffness, N is the number of wires (849), E is the elastic modulus of the titanium alloy wire, A is the cross-sectional area of an individual wire, and L is the length of the wire used to construct the loaded length of the replacement ligament, respectively. The resulting axial stiffness would be approximately 29,500 pounds per inch (5,200 kN/m), about 22 times the mid-range of measured axial stiffness of the natural ACL (1350 pounds per inch, 237 kN/m), making the single bundle of parallel wires far too stiff and not functional as a replacement ligament. Thus, an alternative construction, specifically a braided construction, is needed to decrease the stiffness properties yet maintain sufficient strength properties so that the final replacement ligament more reasonably approximates similar properties of the natural ACL ligament.

For a flat 3-wire or 3-strand braided construction, the length of the individual wires can be estimated using $M=S*[1/\sin^2\alpha+1/\tan^2\alpha]^{1/2}$ where M is the length of the individual wires, S is the loaded length of the braid, and $\alpha$ is the braid angle (41 in FIG. 4), respectively. This formula estimates the length of a wire or strand needed to span the loaded length including the effects due to the overlapping and interleaving of the wires or strands in the braid design. In the present example the 849 wires are now organized into three strands of parallel wires with 283 wires in each strand. Using the formula, the previous loaded length S of 3.25 inches (8.25 cm), and an initial braid angle $\alpha$ of 40 degrees, wires of length 6.37 inches (16.18 cm) are required to construct the loaded length of 3.25 inches (8.25 cm). Additional wire length is needed, beyond the loaded length, to attach braided construction to each of the bones, but this additional length of wire does not figure into the loaded length calculations because it is assumed that the elastic metallic replacement ligament is fixed at or near the tunnel exit points 66 and 67. The length of the wires used in the loaded length primarily impacts the elastic stretch after locking is achieved. The axial stiffness after locking (elastic stretch) can be estimated again using the formula AS=N*E*A/L, where AS is the axial stiffness, N is the number of wires (849), E is the elastic modulus of the titanium alloy wire, A is the cross-sectional area of an individual wire, and L is the length of the wire used to construct the loaded length of the replacement ligament, respectively. The length of wire L used in the axial stiffness formula in this case is the length M calculated using the formula above for the length of wire in a braided construction. Using the axial stiffness formula and the values cited above, the axial stiffness after locking is estimated to be 15,100 pounds per inch (2,600 kN/m). While improved (decreased) relative to the single bundle of parallel wires, this value for axial stiffness is still more than ten times the axial stiffness of the natural ACL, and therefore still not functional for a replacement ligament. The constructional stretch property of the braided construction is needed to further reduce the axial stiffness to the range of the natural ACL.

The axial stiffness in the zone where constructional stretch predominates is less than the axial stiffness in the zone after locking where elastic stretch predominates. Axial stiffness in the zone of constructional stretch is decreased by decreasing the initial braid angle because a smaller initial braid angle will generally provide for more relative motion of the wires or strands as axial tension is applied to the braid. The tension in the wires during the braiding process, the looseness of the braid construction, and the braid pattern, will also impact the axial stiffness in the zone predominated by constructional stretch, as described above. As the braid is placed under increasing tension the initial braid angle will approach the locking angle and the axial elastic properties of the braid will transition to the zone predominated by elastic stretch. Assuming a stiffness ratio of 1:10 for the pre- to post-locking conditions (constructional to elastic stretch) and the previously calculated value for the post-locking condition (elastic stretch), the pre-locking axial stiffness (constructional stretch) would be estimated at around 1,500 pounds per inch (260 kN/m), a value within the stiffness range of the natural ACL ligament in the citations listed above. Experimentation and iteration with the parameters that control the braid properties would be required to fine tune the final properties to the desired levels.

Wires in a bundle or strand as described above do not completely fill the space within the bundle. The percentage of occupied space within a bundle is often described using a number called a packing factor. A packing factor of 90% means that 90% of the space within the bundle or strand is occupied by wires, the remaining 10% being unoccupied space. Using a packing factor of 0.85 for tightly packed round wires, a strand of 283 wires organized in a generally round cross-section would have a diameter of approximately 0.055 inches (1.4 mm). Three such strands would form a 3-strand braided construction with approximate dimensions of 0.16 inches (4.2 mm) wide and 0.11 inches (2.8 mm) high (assuming a width of three times the strand diameter and a height of two times the strand diameter), a very acceptable size for a replacement ACL ligament.

It is noted for completeness that the bending stiffness of a braided construction, such as in the design example, is also much less than the bending stiffness of the single bundle of parallel wires construction using the same number of wires, as described above, assuming that the wires in the single bundle are held together and not allowed to separate during bending. This property of a braided construction is beneficial to the design of elastic metallic replacement ligaments because it allows the elastic metallic replacement ligaments to bend and flex about an axis generally perpendicular to the longitudinal axis of the replacement ligament and not exceed the elastic limits of the metallic wires. In the preferred embodiment, a flat braided design is placed in the body such that the thin aspect of the braid provides maximum bending flexibility as the bones move relative to each other across the joint. For example, the knee joint controls motions predominantly in one plane defined by extension and flexion of the lower leg relative to the upper leg. Thus, a flat braid design for an elastic metallic replacement ligament (ACL) would be placed in the knee such that the replacement ligament had minimum bending stiffness about an axis perpendicular to the above described plane of motion.

The numerical example outlined above is intended to teach and show that it is possible, using a non-obvious combination of braid properties (constructional stretch and elastic stretch) with precise selection of wire materials and dimensions, to achieve a useful range of desired strength and stiffness properties for an elastic metallic replacement ligament for ACL reconstruction. Other examples are possible for elastic metallic replacement ligaments of different lengths, different strengths and stiffness, and for different locations in the body.

While the present elastic metallic replacement ligament has been illustrated and described in detail in the drawings and foregoing description, it is understood that all changes or modifications that come within the spirit of this invention are desired to be protected.

What is claimed is:

1. An elastic replacement ligament for connection between two different bones that include a movable joint therebetween, with one end or a first portion of said elastic replacement ligament attached to one bone on one side of the joint and a second end or a second portion of the elastic replacement ligament attached to a second bone on the other side of the joint, said elastic replacement ligament comprising 3, 4, 5, 6, 8 or 12 strands braided together in a braided construction, wherein each said strand comprises a bundle of multiple metallic wires, each said metallic wire having a diameter or thickness between 0.0005 inches (0.013 mm) and 0.005 inches (0.127 mm); and wherein, the braided construction is configured such that axial yield strength of the braided construction exceeds the axial rupture strength of the natural ligament to be replaced and the axial stiffness of the braided construction is in a range of from one-third to three times the axial stiffness of the natural ligament to be replaced.

2. The elastic replacement ligament of claim 1 wherein said braided construction has a substantially round cross-section.

3. The elastic replacement ligament of claim 1 wherein said braided construction has a substantially flat or rectangular cross-section.

4. The elastic replacement ligament of claim 1 wherein the metallic wires in each said strand are substantially parallel along their lengths.

5. The elastic replacement ligament of claim 1 wherein the metallic wires in each said strand are twisted together.

6. The elastic replacement ligament of claim 1 wherein the metallic wires are made of titanium or titanium alloy.

7. The elastic replacement ligament of claim 6 wherein the metallic wires are made of commercially pure titanium with grades 1, 2, 3, or 4.

8. The elastic replacement ligament of claim 6 wherein the metallic wires are made of a titanium alloy with designations including Ti6Al/4V, Ti6Al/4V ELI, Ti3Al/2.5V, or Ti6Al/7Nb.

9. The elastic replacement ligament of claim 6 wherein the metallic wires are made of a nickel-titanium alloy.

10. The elastic replacement ligament of claim 1 wherein the metallic wires are made of a stainless steel alloy with designations including 302, 303, 304, or 316.

11. The elastic replacement ligament of claim 1 wherein the metallic wires have a generally round cross-section with a diameter between 0.0005 inches (0.013 mm) and 0.005 inches (0.127 mm).

12. The elastic replacement ligament of claim 1 wherein the metallic wires have a generally rectangular cross-section and a thickness between 0.0005 inches (0.013 mm) and 0.005 inches (0.127 mm).

13. The elastic replacement ligament of claim 1 wherein the metallic wires have a generally oval cross-section with a minor diameter between 0.0005 inches (0.013 mm) and 0.005 inches (0.127 mm).

14. The elastic replacement ligament of claim 1 wherein the braided construction passes through a tunnel support sleeve supported in the end of a tunnel in either of the bones.

15. The elastic replacement ligament of claim 1 wherein the braided construction is held under tension and prevented from slipping by a tunnel termination plate attached to one end of said braided construction and to one of the bones.

16. The elastic replacement ligament of claim 15 wherein the tension in said braided construction can be modified by adjusting the placement of and locking said braided construction in or to said tunnel termination plate.

17. The elastic replacement ligament of claim 1 wherein each said strand comprises three or more of the metallic wires braided together.

18. An elastic replacement ligament for connection between two different bones that include a movable joint therebetween, with one end or a first portion of said elastic replacement ligament attached to one bone on one side of the joint and a second end or a second portion of the elastic replacement ligament attached to a second bone on the other side of the joint, said elastic replacement ligament made of strands of metallic wires, where said strands are bundles of more than one metallic wire with each said metallic wire having a diameter or thickness between 0.0005 inches (0.013 mm) and 0.005 inches (0.127 mm), where said strands are arranged in a braided construction comprising 3, 4, 5, 6, 8, or 12 strands, and where the braided construction is configured such that the axial yield strength of the braided construction exceeds the axial rupture strength of the natural ligament to be replaced and the axial stiffness of the braided construction is in the range between one-third to three times the axial stiffness of the natural ligament to be replaced.

19. The elastic replacement ligament of claim 1 wherein the yield strength of the braided construction exceeds 1725 Newtons and the axial stiffness of the braided construction is in a range of from 61 to 876 kiloNewtons per meter.

20. The elastic replacement ligament of claim 18 wherein each said strand comprises three or more of the metallic wires braided together.

21. The elastic replacement ligament of claim 18 wherein said braided construction of strands has a substantially round cross-section.

22. The elastic replacement ligament of claim 18 wherein said braided construction of strands has a substantially flat or rectangular cross-section.

23. The elastic replacement ligament of claim 18 wherein the metallic wires are arranged in each said strand such that the metallic wires are substantially parallel along their lengths.

24. The elastic replacement ligament of claim 18 wherein the metallic wires are arranged in each said strand such that the metallic wires are twisted together.

25. The elastic replacement ligament of claim 18 wherein the metallic wires are made of titanium or titanium alloy.

26. The elastic replacement ligament of claim 25 wherein the metallic wires are made of commercially pure titanium with grades 1, 2, 3, or 4.

27. The elastic replacement ligament of claim 25 wherein the metallic wires are made of a titanium alloy with designations including Ti6Al/4V, Ti6Al/4V ELI, Ti3Al/2.5V, or Ti6Al/7Nb.

28. The elastic replacement ligament of claim 25 wherein the metallic wires are made of a nickel-titanium alloy.

29. The elastic replacement ligament of claim 18 wherein the metallic wires are made of a stainless steel alloy with designations including 302, 303, 304, or 316.

30. The elastic replacement ligament of claim 18 wherein the metallic wires have a generally round cross-section with a diameter between 0.0005 inches (0.013 mm) and 0.005 inches (0.127 mm).

31. The elastic replacement ligament of claim 18 wherein the metallic wires have a generally rectangular cross-section and a thickness between 0.0005 inches (0.013 mm) and 0.005 inches (0.127 mm).

32. The elastic replacement ligament of claim 18 wherein the metallic wires have a generally oval cross-section with a minor diameter between 0.0005 inches (0.013 mm) and 0.005 inches (0.127 mm).

33. The elastic replacement ligament of claim 18 wherein the braided construction passes through a tunnel support sleeve supported in the end of a tunnel in either of the bones.

34. The elastic replacement ligament of claim 18 wherein the braided construction is held under tension and prevented from slipping by a tunnel termination plate attached to one end of said braided construction and to one of the bones.

35. The elastic replacement ligament of claim 34 wherein the tension in said braided construction can be modified by adjusting the placement of and locking said braided construction in or to said tunnel termination plate.

36. A method for replacement of a natural ligament between two bones with a joint therebetween, the method comprising:
    attaching a first portion of an elastic replacement ligament to one bone on one side of the joint and a second portion of the elastic metallic replacement ligament to a second bone on the other side of the joint;
    said elastic replacement ligament comprising 3, 4, 5, 6, 8 or 12 strands braided together in a braided construction, wherein each said strand comprises a bundle of multiple metallic wires, each said metallic wire having a diameter or thickness between 0.0005 inches (0.013 mm) and 0.005 inches (0.127 mm); and
    wherein, the braided construction is configured such that axial yield strength of the braided construction exceeds the axial rupture strength of the natural ligament to be replaced and the axial stiffness of the braided construction is in a range of from one-third to three times the axial stiffness of the natural ligament to be replaced.

37. The method of claim 36, comprising disposing at least a portion of the braided construction in a tunnel support sleeve supported in the end of a tunnel in either of the first bone or the second bone.

38. The method of claim 36, wherein the attaching comprises attaching a tunnel termination plate to the first portion of the braided construction and the first bone or attaching the tunnel termination plate to the second portion of the braided construction and the second bone.

39. The method of claim 36, comprising passing the braided construction through a first tunnel through the first bone and through a second tunnel through the second bone.

40. The method of claim 36, wherein as attached to the first bone and the second bone during the attaching:
    the braided construction passes through a first tunnel through the first bone and a through a second tunnel through the second bone; and
    the braided construction passes through a first tunnel support sleeve disposed in the first tunnel and through a second tunnel support sleeve disposed in the second tunnel.

41. The method of claim 40, wherein the attaching comprises: holding the braided construction in tension by a tunnel termination plate attached to the braided construction and to the first bone or the second bone.

* * * * *